US011186856B2

(12) United States Patent
Haseltine et al.

(10) Patent No.: US 11,186,856 B2
(45) Date of Patent: Nov. 30, 2021

(54) **MULTIMERS OF *S. SOLFATARICUS* SINGLE-STRANDED DNA-BINDING PROTEIN AND METHODS OF USE THEREOF**

(71) Applicant: The Regents of the University of California, Oakland, CA (US)

(72) Inventors: Cynthia A. Haseltine, Davis, CA (US); Stephen Kowalczykowski, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/173,963

(22) Filed: Oct. 29, 2018

(65) Prior Publication Data

US 2019/0119714 A1    Apr. 25, 2019

Related U.S. Application Data

(63) Continuation of application No. 12/941,761, filed on Nov. 8, 2010, now abandoned, which is a continuation of application No. 10/386,575, filed on Mar. 11, 2003, now abandoned.

(51) Int. Cl.
*C12Q 1/686* (2018.01)
*C12P 19/34* (2006.01)
*C07K 14/195* (2006.01)

(52) U.S. Cl.
CPC ............ *C12P 19/34* (2013.01); *C07K 14/195* (2013.01); *C12Q 1/686* (2013.01)

(58) Field of Classification Search
None
See application file for complete search history.

(56) References Cited

U.S. PATENT DOCUMENTS

| | | |
|---|---|---|
| 5,449,603 A | 9/1995 | Nielson et al. |
| 5,605,824 A | 2/1997 | Nielson et al. |
| 5,646,019 A | 7/1997 | Nielson et al. |
| 5,773,257 A | 9/1998 | Nielson et al. |
| 6,503,729 B1 | 1/2003 | Bult et al. |
| 6,852,832 B1 | 2/2005 | Kowalczykowski et al. |

OTHER PUBLICATIONS

GenBank Accession No. AAK42515 NCBI website Jul. 5, 2001.
Bochkarev, et al. "Structure of the single-stranded-DNA-binding domain of replication protein A bound to DNA." Nature 385, No. 6612 (1997) 176.Ochkarev, A., *Nature* 385, 176-181 (1997).
Bochkareva, et al. "The RPA32 subunit of human replication protein A contains a single-stranded DNA-binding domain." Journal of Biological Chemistry 273, No. 7 (1998): 3932-3936.
Bult, et al., "Complete genome sequence of the methanogenic archaeon, Methanococcus jannaschii." Science 273, No. 5278 (1996): 1058-1073.
Bult, et al., NCBI, National Library of Medicine, NIH (Bethesda, MD, USA) Accession No. F64444, Sep. 1996.
Carpentieri, et al. "Physical and functional interaction between the mini-chromosome maintenance-like DNA helicase and the single-stranded DNA binding protein from the crenarchaeon Sulfolobus solfataricus." Journal of Biological Chemistry 277, No. 14 (2002): 12118-12127.
Chedin, F., et al., "Novel homologs of replication protein A in Archaea: implications for the evolution of ssDNA-binding proteins," *TIBS*, Aug. 1998, vol. 23, pp. 273-277.
Cubeddu, L., et al., "Structural and functional characterization of *Solfolobus solfactaricus* SSB and its interaction with DNA," *FASEB Summer Research*, 2002, Poster Abstract, 1 pg.
Cubeddu, L., et al., "Structural and calorimetric studies of an archaeal single-stranded DNA binding protein," European Conference on Current Trends in Microcalorimetry: Applications of Biocalorimetry (ABC III), Aug. 27-30, 2002, Dublin, Ireland, Abstract, 1 pg.
Fairman, et al. "Cellular factors required for multiple stages of SV40 DNA Yeplication in vitro." The EMBO Journal 7, No. 4 (1988): 1211-1218.
Gomes, et al. "Functional domains of the 70-kilodalton subunit of human replication protein A." Biochemistry 35, No. 32 (1996): 10558-10568.
Haseltine, C., et al., "A distinctive single-stranded DNA binding protein from the Archaeon *Sulfolobus solfataricus*," *Molecular Microbiology*, 2002, vol. 43, No. 6, pp. 1505-1515.
Henricksen, et al. "Phosphorylation of human replication protein A by the DNA-dependent protein kinase is involved in the modulation of DNA replication." Nucleic acids research 24, No. 15 (1996): 3107-3112.
Kelly, et al., Identification and characterization of a single-stranded DNA-binding protein from the archaeon Methanococcus jannaschii, PNAS Dec. 8, 1998 95(25) 14634-14639.
Kerr, I., et al., "Overexpression, purification, crystallization and data collection of a single-stranded DNA-binding protein from Sulfolobus solfataricus," Acta Cryst., 2001, vol. D57, pp. 1290-1292.
Kerr, et al., "Insights into ssDNA recognition by the OB fold from a structural and thermodynamic study of Sulfolobus SSB protein." The EMBO journal 22, No. 11 (2003): 2561-2570.
Kim et al., Interactions of Human Replication Protein A with Oligonucleotides, Biochemistry, 33:14197-206 (1994).
Kim et al., Biding Properties of Replication Protein A from Human Yeast Cells, Mol. Cell Biol., 12:3050-3059 (1992).
Klenk, H. P. et al., The Complete Genome Sequence of the Hyperthermophilic, Suklphate-Reducing Achaeon Archaeoglobus Fulgidus, Nature 390, 364-370 (1997).
Lin, et al. "The evolutionarily conserved zinc finger motif in the largest subunit of human replication protein A is required for DNA replication and mismatch repair but not for nucleotide excision repair." Journal of Biological Chemistry 273, No. 3 (1998): 1453-1461.

(Continued)

*Primary Examiner* — Katherine D Salmon
(74) *Attorney, Agent, or Firm* — Kilpatrick Townsend & Stockton LLP

(57) ABSTRACT

The invention provides multimers of *S. solfataricus* ssDNA binding protein that bind single stranded DNA. The multimers are robust and stable reagents for use in PCR and other techniques for engineering DNA. The invention further provides methods for performing nucleic acid amplification and engineering using the multimers.

12 Claims, 8 Drawing Sheets

Specification includes a Sequence Listing.

(56) References Cited

OTHER PUBLICATIONS

Lohman, et al. "*Escherichia coli* single-stranded DNA-binding protein: multiple DNA-binding modes and cooperativities." Annual review of biochemistry 63, No. 1 (1994): 527-570.
Philipova, D. ef al., A Hierarchy of SSB Protomers in Replication Protein A, *Genes Dev.* 10, 2222-2233 (1996).
Sancar, A., et al., Sequences of the SSB Gene and Protein, *Proc. Natl. Acad. Sci. USA* 78, 4274-4278 (1981).
Shamoo, et al. "Crystal structure of a replication fork single-stranded DNA binding protein (T4 gp32) complexed to DNA." Nature 376, No. 6538 (1995): 362.
She, et al., "The complete genome of the crenarchaeon Sulfolobus solfataricus P2," PNAS, Jul. 3, 2001, vol. 98, No. 14, pp. 7835-7840.
Sreenivas, et al. "An archaeal DNA binding protein from thermophilic Sulfolobus acidocaldarius forms different types of complexes with DNA." IUBMB Life 44, No. 2 (1998): 269-282.
Smith, et al. "Complete genome sequence of Methanobacterium thermoautotrophicum deltaH: functional analysis and comparative genomics." Journal of bacteriology 179, No. 22 (1997): 7135-7155.
Wadsworth, et al. "Identification and properties of the crenarchaeal single-stranded DNA binding protein from Sulfolobus solfataricus." Nucleic Acids Research 29, No. 4 (2001): 914-920.

Figure 1

```
                                x    x    xxxx  x       x x   x x   xx xxxx
S.solfataricus SSB    1    MEEKVGNLKPNMESVNTVRLLEASEARQQTKNGVRTIS..EAIVGDET  48
A. pernix SSB         1      MLLREGLRNVSISGRGLETGEPKMVETSRGPATLS..EAVVGDES  43
M. jannachii RPA     69    ISLIFEGQIGVELTGVITDISEIKTFKRDGSLGKYK.RITTADKS 113
S. cerevisiae RPA70 301    NFIKLDAIQNQEVNSNVDLLGILQTINPHFELTSRAG.KKFDRRDITLVDDS 351
H. sapiens RPA70    301    DFTGIDDLENKSKDSLVDIISICKSYEEATKITVRSNNREVAKRNIYLMDTS 352
                                                               *  *   *
Consensus                  ..........e....V.i.g......e......r.g........i...D.s xx xx xxxx xxx xx  xx   x xx xxxx    x xx x x       x
S. solfataricus SSB  49    GR.VKLTLWGKHAGSIK..EGQVVKIENAWTIAEKGQVQLNAGSKTKI 93
A. pernix SSB        44    GR.VKVTLWGSHAGTLK..EGEAVRIEGAWTTSYRGKVQVNVGRESTI 88
M. jannachii RPA    114    GT.IRMTLWDDLA.ELDVKVGDVIKIERARARKWRNNLELSSTSETKI 159
S. cerevisiae RPA70 352    GFSISVGLWNQQALDFNLPEGSVAAIKGVRVIDEGGKSLSMGFSSTLI 399
H. sapiens RPA70    353    GKVVTATLWGEDADKFDGSRQPVLAIKGARVSDEGGRSLSVLSSSTII 400
                                 * *                 *   *   **    **
Consensus                  G..v..tLWg..A......eg.v..Ie.ar.t.f.g.......s.t.I
```

FIGURE 8A

SEQ ID NO:1

```
  1  MEEKVGNLKP NMESVNVTVR VLEASEARQI QTKNGVRTIS EAIVGDETGR VKLTLWGKHA
 61  GSIKEGQVVK IENAWTTAFK GQVQLNAGSK TKIAEASEDG FPESSQIPEN TPTAPQQMRG
121  GGRGFRGGGR RYGRRGGRRQ ENEEGEEE
```

FIGURE 8B

SEQ ID NO:2

```
  1   atggaagaaa aagtaggtaa tctaaaacca aatatggaaa gcgtaaatgt aaccgtaaga
 61   gttttggaag caagcgaagc aagacaaata cagacaaaga acggtgttag aacaatcagt
121   gaggctattg ttggagatga aacgggaaga gtaaagttaa cattatgggg aaaacatgca
181   ggtagtataa aagaaggtca agtggtaaag atagaaaacg cgtggaccac cgcttttaag
241   ggtcaagtac agttaaatgc tggaagcaaa actaagatag ctgaagcttc agaagatgga
301   tttccagaat catctcaaat accagaaaat acaccaacag ctcctcagca aatgcgtgga
361   ggaggaagag gattccgcgg tgggggaaga aggtatggaa gaagaggtgg tagaagacaa
421   gaaaacgaag aaggtgaaga ggagtga
```

MULTIMERS OF *S. SOLFATARICUS* SINGLE-STRANDED DNA-BINDING PROTEIN AND METHODS OF USE THEREOF

CROSS-REFERENCES TO RELATED APPLICATIONS

This application is a continuation of U.S. patent application Ser. No. 10/386,575, filed Mar. 11, 2003, the entire contents of which is incorporated herein by reference.

STATEMENT AS TO RIGHTS TO INVENTIONS MADE UNDER FEDERALLY SPONSORED RESEARCH AND DEVELOPMENT

This invention was made with government support under Grant (or Contract) No. GM62653 awarded by the National Institutes of Health and Grant (or Contract) No. 0074380 awarded by the National Science Foundation. The government has certain rights in this invention.

REFERENCE TO A "SEQUENCE LISTING," A TABLE, OR A COMPUTER PROGRAM LISTING APPENDIX SUBMITTED ON A COMPACT DISK.

NOT APPLICABLE

FIELD OF THE INVENTION

This invention relates to single stranded DNA binding proteins that are robust reagents for use in nucleic acid amplification reactions.

BACKGROUND OF THE INVENTION

Single-stranded DNA (ssDNA) binding proteins (SSBs) are essential in most intracellular interactions that involve DNA, including replication, repair, and recombination (Kowalczykowski, S. C. et al., *Microbiol Rev* 58:401-465 (1994); Lohman, T. M. et al., *Annu Rev* Biochem 63:527-570 (1994) ("Lohman 1994")). Homologues of this class of proteins were identified in all three domains of life, as well as in viral genomes (Chedin, F. et al., *Trends Biochem Sci* 23:273-277 (1998) ("Chedin 1998"); Iftode, C. et al., *Crit Rev Biochem Mol Biol* 34:141-180 (1999); Kelly, T. J. et al., *Proc Natl Acad Sci USA* 95:14634-14639 (1998); Kowalczykowski, S. C. et al., *Single-stranded DNA binding proteins*. in The Enzymes. Boyer, P.D. (ed.) New York: Academic Press, pp. 373-442 (1981); Lohman 1994; Wold, M. S. *Annu Rev Biochem* 66:61-92 (1997)). Despite the lack of strong homology at the amino acid level, preservation of both structural and domain organization suggests that SSBs are derived from a common evolutionary ancestor (Chedin 1998; Pfuetzner, R. A. et al., *J Biol Chem* 272:430-434 (1997); Raghunathan, S. et al., *Nat Struct Biol* 7:648-652 (2000)). While functionally equivalent, eubacterial SSB and the eukaryotic version, RPA, have distinctly different quaternary structures. In eubacteria, SSB is encoded by a single gene and the active form of the protein is a homotetramer in which each monomer provides one ssDNA-binding domain (Lohman 1994). In eukaryotes, the RPA complex from both humans and yeast is composed of three distinct subunits which together provide a total of four ssDNA-binding domains (Brill, S. J. et al., *Mol Cell Biol* 18:7225-7234 (1998)).

Archaea are a separate group of organisms distinguished from the eubacteria through 16S rDNA sequence analysis. These prokaryotes are further subdivided into three diverse groups named the crenarchaeota, the euryarchaeota, and the korarchaeota (Barns, S. M. et al., *Proc Natl Acad Sci USA*, 93:9188-9193 (1996); Woese, C. R. et al., *Proc Natl Acad Sci USA* 87:4576-4579 (1990); Woese, C. R. et al., *Proc Natl Acad Sci USA* 74:5088-5090 (1977)). Only members of the crenarchaeal and euryarchaeal groups, however, have been cultivated. Genomic studies suggest a significant evolutionary division between metabolic and informational processes in archaea. While most intermediary metabolic processes strongly resemble those observed in eubacteria, genomic informational processes are generally thought to be more closely related to those found in eukaryotes (reviewed in (Doolittle, W. F. et al., *Curr Biol* 8:R209-211 (1998))).

Archaea utilize eukaryotic B-type DNA polymerases for replication, and their ribosomal proteins, as well as translation initiation factors, are remarkably eukaryotic. The recent identification of archaeal snoRNA genes reveals an unexpected eukaryotic connection (Omer, A. D. et al., *Science* 288:517-522 (2000)). Transcription also involves eukaryotic protein homologues, but the discovery of multiple TBP and TFB proteins in halophiles hints at a unique archaeal transcription mechanism (Baliga, N. S. et al., *Mol Microbiol*, 36:1184-1185 (2000)). Examination of archaeal recombination proteins suggests a definite similarity with eukaryotes. The archaeal DNA strand exchange protein RadA is more similar to its eukaryotic counterpart, Rad51 protein, than to the eubacterial RecA protein, both at the amino acid level (Sandler, S. J. et al., *J Bacteriol* 181:907-915 (1999)) and at the biochemical level (Seitz, E. M. et al., *Genes Dev* 12:1248-1253 (1998)). The associated RadB protein is proposed to serve as a simpler archaeal version of eukaryotic Rad55/57 protein (DiRuggiero, J. et al., *J Mol Evol* 49:474-484 (1999); Komori, K. et al., *J Biol Chem* 275:33782-33790 (2000); Rashid, N. et al., *Mol Gen Genet* 253:397-400 (1996)), and archaeal Holliday junction resolvase protein characterization suggests they may also be eukaryotic in nature (Komori, K. et al., *Proc Natl Acad Sci USA* 96:8873-8878 (1999); Kvaratskhelia, M. et al., *J Mol Biol* 297:923-932 (2000)).

Recent descriptions of archaeal SSB homologues from the euryarchaeal branch of the archaeal domain demonstrate their amino acid sequences are more similar to eukaryotic RPA than to eubacterial SSB (Chedin 1998; Kelly, T. J. et al., *Proc Natl Acad Sci USA* 95:14634-14639 (1998)). However, these archaeal proteins maintain multiple ssDNA-binding domains within one or just a pair of polypeptides and therefore, are expected to function as monomers or heterodimers rather than as a homotetramer (as does *E. coli* SSB). It was proposed that these archaeal RPA homologues are evolutionarily related to eukaryotic RPA through gene duplication and recombination events (Chedin 1998).

Genome sequencing of several archaeons simplified molecular analysis in these organisms. While a number of euryarchaeal genome sequences have been determined, to date the only publicly available crenarchaeal genome sequences are that of *Aeropyrum pernix* (Kawarabayasi, Y. et al., *DNA Res* 6:83-101:145-152 (1999)) and *Sulfolobus solfataricus* (She, Q. et al., *Proc Natl Acad Sci USA* 98:7835-7840 (2001)). In 2001, Wadsworth and White described the identification of an ssDNA binding protein from *S. solfataricus*. Wadsworth and White, Nuc Acids Res 29(4):914-920 (2001).

BRIEF SUMMARY OF THE INVENTION

This invention provides isolated multimers, wherein each unit of said multimer has at least 70% sequence identity to SEQ ID NO:1, and wherein the multimer binds single stranded DNA. In some embodiments, each unit of the multimer has at least 80% sequence identity to SEQ ID NO:1. In other embodiments, each unit of the multimer has at least 90% sequence identity to SEQ ID NO:1. The invention further provides embodiments wherein each unit has the sequence of SEQ ID NO:1. In some preferred embodiments, the multimer is a tetramer.

In another important group of embodiments, the invention provides methods of performing nucleic acid amplification, said method comprising contacting a single stranded DNA with a multimeric protein, wherein each unit of the multimeric protein has at least 70% sequence identity to SEQ ID NO:1, and wherein said multimer binds single stranded DNA. In some of these embodiments, each unit of the multimeric protein has at least 80% sequence identity to SEQ ID NO:1, while in others, each unit of the multimeric protein has at least 90% sequence identity to SEQ ID NO:1. In some embodiments, each unit of the multimeric protein has the sequence of SEQ ID NO:1. The nucleic acid amplification can be, for example, polymerase chain reaction, ligase chain reaction, transcription-based amplification system, and self-sustained sequence replication system. In some embodiments, the method of nucleic acid amplification is polymerase chain reaction.

The invention further provides methods for performing nucleic acid engineering, comprising contacting single stranded DNA with a multimeric protein, wherein each unit of the multimeric protein has at least 70% sequence identity to SEQ ID NO:1, and wherein said multimer binds single stranded DNA. In some of these embodiments, each unit of the multimeric protein has at least 80% sequence identity to SEQ ID NO:1, while in others, each unit of the multimeric protein has at least 90% sequence identity to SEQ ID NO:1. In some embodiments, each unit of the multimeric protein has the sequence of SEQ ID NO:1. The nucleic acid engineering can be, for example, PCR-based DNA sequencing, recombination mediated cloning, PCR-mediated gene replacement, PCR-mediated recombination, RT-PCR cDNA synthesis, and in vitro sequence mutagenesis.

BRIEF DESCRIPTION OF THE DRAWINGS

FIG. 1. Alignment of ssDNA-binding domain protein sequences. Crenarchaeal sequences are aligned with the first ssDNA-binding domains of *M. jannachii* RPA (SEQ ID NO:5), *S. cerevisiae* RPA70 (SEQ ID NO:6), and *H. sapiens* RPA70 (SEQ ID NO:7). Identical residues are shaded black and conserved residues are shaded gray. The * symbol indicates residues identified in the *H. sapiens* RPA70 that interact with DNA (Bochkarev, A. et al., *Nature*, 385:176-181 (1997)), while an x indicates residues that are identical between the two crenarchaeal sequences. The consensus is shown beneath the alignment. Sequence accession numbers are as follows: *S. solfataricus* SSB (portion shown in Figure is SEQ ID NO:3), SSO2364; *A. pernix* SSB (portion shown in Figure is SEQ ID NO:4), gi5105001; *M jannachii* RPA, MJ1159; *S. cerevisiae* RPA70, gi6319321; *H. sapiens* RPA70, gi1350579.

FIG. 4A. Elution of purified SsoSSB protein relative to molecular weight standards: BSA (66 kDa), carbonic anhydrase (29 kDa), and cytochrome C (12.4 kDa), which are represented by closed squares. Ve/Vo, elution volume divided by void volume. FIG. 4B. A representative elution profile for purified SsoSSB protein. Closed squares represent optical density at 280 nm ($OD_{280}$) for the elution volume indicated.

FIG. 6A. Optical densities were monitored spectrophotometrically at 600 nm. FIG. 6B. Colony forming units (cfu) were determined by plating in triplicate and the points shown are averages of the replicates.

FIG. 7A. A schematic representation of the formation of nicked circular dsDNA and joint molecules from starting substrates. FIG. 7B. Photo of gel. Lane 1, no protein; lane 2, RecA protein; lane 3, RecA protein and SsoSSB protein; lane 4, RecA protein and *E. coli* SSB protein. The abbreviations are: JM, joint molecules; NC, nicked circular dsDNA; DS, dsDNA; and SS, ssDNA.

FIGS. 8A and 8B. FIG. 8A sets forth the amino acid sequence of SsoSSB protein. FIG. 8B sets forth the nucleotide sequence encoding SsoSSB protein.

DETAILED DESCRIPTION

I. Introduction

Figure 2:
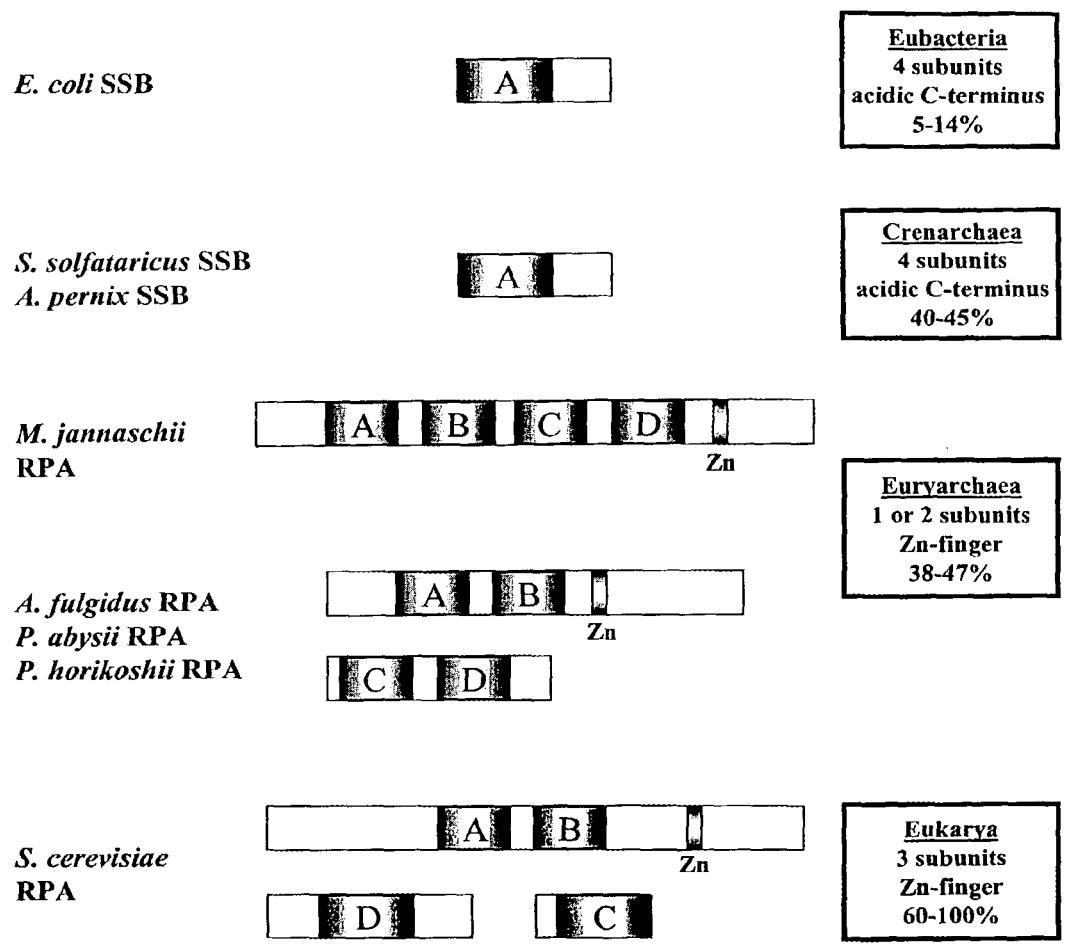
FIG. 2. Schematic representation of the domainal architecture of ssDNA-binding proteins in all three domains of life. Homologous DNA-binding domains are represented by shaded boxes and the location of the zinc-finger motif is indicated. A summary of the attributes of each type of ssDNA-binding protein is represented in the boxes. A range of percentage similarities for proteins from each domain to the first single-stranded DNA-binding domain of *S. cerevisiae* RPA70 were determined using the BestFit program and are indicated.

The crenarchaeon *S. solfataricus* is a hyperthermophic aerobe that grows in sulfur hot springs. Its optimal growth conditions are temperatures of 70-90° C. and pH levels from 2-4. The entire genome of the organism was sequenced and published in 2001. She et al., "The complete genome of the crenarchaeon *Sulfolobus solfataricus* P2," *Proc. Natl Acad Sci* (USA) 98:7835-7840 (2001). In 2001, Wadsworth and White reported the identification of a single-stranded DNA (ssDNA) binding protein (SSB) from *S. solfataricus*. Wadsworth and White, Nuc Acids Res 29(4):914-920 (2001). The work from this laboratory indicates that the SSB is present as a monomer.

The *S. solfataricus* ssDNA binding protein ("SsoSSB protein") consists of 148 amino acids with 47% identity and 69% similarity (that is, that the residues are either identical or conservative substitutions for one another) to the SSB of another crenarchaeon, *A. pernix*. The amino acid sequence of SsoSSB (SEQ ID NO:1) is shown in FIG. 8A, and is available in the National Center for Biotechnology Information Entrez database under accession numbers NP_343725 and AAK42515.

Surprisingly, it has been discovered that the monomers of *S. solfataricus* ssDNA binding protein ("SsoSSB protein") associate with one another to form a complex, referred to herein as "multimeric protein" or a "multimer") in solution and it is the complex, or multimeric protein, that is functional in binding ssDNA. The multimeric proteins are, however, composed of monomers of the SsoSSB protein. The multimers are comprised of multiples of 2. It is believed that the multimers are not composed of more than 24 monomers of SsoSSB, and are more commonly composed of 12 or fewer. Data from the studies reported in the Examples indicates that SsoSSB is present in solution primarily as dimers and tetramers, with tetramers being the prevalent multimeric form present. The most active form of the protein is therefore a homotetramer in which each monomer provides one ssDNA-binding domain. While *S. solfataricus* SSB has no sequence homology to the *E. coli* SSB protein, it therefore physically acts more like the SSB found in eubacteria, which multimerize, than like those found in eukaryotes and the SSB of other archaeons identified to date.

Accordingly, the present invention provides multimers comprising monomers of single stranded DNA binding protein of *S. solfataricus* or of defined variations of the SsoSSB protein that retain the ability to bind ssDNA. In preferred forms, the multimer is a dimer (that is, an assembly of two monomers) or a tetramer (that is, an assembly of four monomers), with the tetramer form being the most preferred. The multimers function to bind ssDNA.

II. Uses of the SSDNA-Binding Proteins of the Invention

Members of the Archaea typically live in conditions of extreme heat, pH, or salt concentrations. Thus, they offer a source of enzymes and other proteins which can be useful reagents in assays and other commercial reactions. As noted above, the crenarchaeon *S. solfataricus* grows optimally at temperatures between 70-90° C. Thus, its proteins are particularly adapted for use at temperatures which are high for reagents originating from biological sources. More specifically, the DNA replication of *S. solfataricus* takes place at high temperature. But, the multimers are active over a wide range of temperatures, and can be used at temperatures as low as 37° C. to as high as 65° C. and even as high as 90° C.

During polymerase chain reaction (PCR), this activity permits DNA polymerase to replicate more of the DNA template strand in each PCR cycle than would be replicated in the absence of the protein, thereby increasing yield. Moreover, temperature-resistant proteins such as SsoSSB protein multimers are not inactivated by the temperature cycling which is part of the PCR process, and thus do not have to be replaced before the next reaction can proceed. This enhances the ability to automate the procedures. Thus, use of heat-resistant ssDNA-binding proteins, like the multimers provided here, not only increases the yield of each PCR cycle, but also permits automation of the overall process and the speed with which cycles can be conducted.

Additionally, archaeal proteins are much more stable than most eukaryotic and bacterial proteins. For example, SSB protein from *E. coli* must be stored at −80° C. If refrigerated, it loses some or all of its activity within a month and at room temperature, it loses some or all of its activity within 72 hours. By contrast, SsoSSB retains its activity at room temperature for at least three weeks, and can be refrigerated for over a year without loss of activity. The stability of the protein therefore makes it convenient for use even in protocols in which high temperatures are not required.

SsoSSB protein multimers are therefore robust reagents useful for a variety of biotechnical applications involving amplification or engineering of nucleic acids, or both. The multimers are expected to be useful in a number of such techniques well known in the art, such as PCR, ligase chain reaction, transcription-based amplification system, self-sustained sequence replication system, PCR-based DNA sequencing, recombination mediated cloning, PCR-mediated gene replacement, PCR-mediated recombination, reverse transcriptase (RT)-PCR cDNA synthesis, and in vitro sequence mutagenesis. For convenience, techniques which employ the binding of ssDNA in the course of manipulating nucleic acids, such as PCR-based DNA sequencing, recombination mediated cloning, PCR-mediated gene replacement, PCR-mediated recombination, reverse transcriptase (RT) -PCR cDNA synthesis, and in vitro sequence mutagenesis, are sometimes referred to herein as "nucleic acid engineering."

III. Modifications of *S. solfataricus* SSDNA Binding Protein Multimers

It is understood that the *S. solfataricus* ssDNA binding protein can be modified and still retain the desired robustness and ssDNA binding function. In some embodiments, the amino acid sequence has at least 70% identity to that of SEQ ID NO:1. In other embodiments, the amino acid sequence has 75%, 80%, 85%, 90%, 91%, 92%, 93%, 94%, 95%, 96%, 97%, 98% or even 99% identity to SEQ ID NO:1 (with each increasing percentage of identity being more preferred), and retains the ability to bind ssDNA.

It should be noted that the monomers composing a particular multimer need not be exact duplicates of one another. Thus, while a dimer or a tetramer of the invention is for convenience considered a homodimer or a homotetramer, the monomers of the dimer or tetramer may not be precisely identical. In a given tetramer, for example, one monomer might have the native sequence of SEQ ID NO:1, the second monomer might have a conservative substitution compared to the native sequence (SEQ ID NO:1) and the third and fourth monomers might have only 80% and 90% sequence identity, respectively, to the native sequence. Or, all four monomers of the tetramer might be close to the sequence of SEQ ID NO:1, but each might have several conservative substitutions of residues of SEQ ID NO:1. Or, all four monomers might have the same two conservative substitutions and otherwise have the sequence of SEQ ID NO:1, or all four might have the sequence of native SEQ ID NO:1, in which case all the monomers are identical to one another. Whatever the exact composition of the individual monomers, however, it is important is that the multimer they form retains the desired ability to bind ssDNA.

Persons of skill are also aware that ssDNA binding proteins typically contain a motif known as an oligonucleotide/oligosaccharide binding ("OB")-fold". OB-fold proteins are a superfamily of proteins having common structural features; both the superfamily and the common structural features are well known in the art. See, e.g., Callebaut and Mornon, Biochem J 321:125-32 (1997). Williamson et al., Biochemistry 33:11745-59 (1994) summarize some of these features: "[t]he common structural features include the number of beta-strands and their arrangement, the beta-barrel shear number, an interstrand hydrogen bond network, the packing of the hydrophobic core, and a conserved beta-bulge." One feature of ssDNA binding, OB-fold proteins is the presence of a channel in the protein so sized as to permit binding of ssDNA along the channel. As noted by Bochkarev et al., Nature 385:176-81 (1997): "[t]he ssDNA lies in a channel that extends from one subdomain to the other." For ease in visualization, the protein channel is sometimes described in the art as similar in conformation to a hand curled around a glass.

SsoSSB protein is a monomer, which contains an OB-fold between residues 32-71. The monomers assemble into a multimer with structural features typical of OB-fold proteins which bind ssDNA. Multimers of SsoSSB proteins form a channel so sized as to permit binding of the ssDNA along the channel. The carboxyl terminus of the protein monomers also contains a number of acidic residues.

FIG. 1 shows an alignment of SsoSSB protein with other OB-fold ssDNA binding proteins. As noted in the Description of FIG. 1, the SsoSSB residues shown on a black background are identical among these proteins. These residues can be assumed to be important for protein function and their substitution in an SsoSSB monomer is therefore generally less favored. As also noted in the Description of FIG. 1, residues shown on a gray background are conservative substitutions among the proteins. Thus, it is expected that other conservative substitutions of these residues in an SsoSSB monomer will likely result in a functional ssDNA binding proteins multimer. The residues shown in FIG. 1 on a normal, white background are not conserved among the various ssDNA binding proteins aligned in the Figure; these residues can generally undergo substitution. In preferred embodiments, the substitutions are conservative substitutions. Substitutions can also generally be made outside of the OB-fold region defined by residues 32-71. Any particular substitution can be readily tested, for example by the assays set forth in the Examples, to confirm that the substitution does not decrease the ability to bind ssDNA below any particular degree chosen by the practitioner.

Preferably, a multimer containing the modified protein retains at least 50% of the ability of a multimer of native *S. solfataricus* SSB to bind DNA. More preferably, a multimer containing the modified protein has at least 60%, 65%, 70% 75%, 80%, 85%, 90%, 95% or even more of the ability of a multimer of native *S. solfataricus* SSB to bind ssDNA, as measured in such assays. Gel-shift assays provide especially convenient methods of determining the degree to which any particular modified SsoSSB protein multimer retains the ability of a native SsoSSB protein multimer to bind single stranded DNA. Many other such assays are, however, known in the art and can be used at the practitioner's choice. For example, the multimers can be permitted to bind ssDNA and the fluorescence of the proteins examined by spectrophotometry. Higher degrees of binding are detected by decreased fluorescence as more amino acids of the proteins are blocked by the DNA.

Although the discussion above refers to substitutions of the native SsoSSB sequence, SEQ ID NO:1, persons of skill will be aware that it is not necessary to first synthesize or express the protein and then to modify it. Typically, the practitioner decides on the substitution or substitutions desired, and assembles a nucleic acid vector that when expressed in a suitable host cell, such as *E. coli*, results in a protein with the desired sequence. Kits for engineering plasmids containing desired nucleic acid inserts and expressing such vectors in host cells are commercially available from a number of venders, and are well known in the art.

The terms "identical" or percent "identity," in the context of two or more polypeptide sequences, refer to two or more sequences or subsequences that are the same or have a specified percentage of amino acid residues that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988), e.g., as implemented in the program PC/GENE (Intelligenetics, Mountain View, Calif., USA).

As noted, one type of substitution is termed a "conservative substitution." One of skill will recognize that individual substitutions, in a peptide, polypeptide, or protein sequence which alters a single amino acid or a small percentage of amino acids in the encoded sequence are "conservatively modified variants" where the alteration results in the substitution of an amino acid with a chemically similar amino acid. Conservative substitution tables providing functionally similar amino acids are well known in the art. The following six groups each contain amino acids that are generally considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

The phrase "substantially identical," in the context of two polypeptides, refers to sequences or subsequences that have at least 60%, preferably 70%, more preferably 80%, most preferably 90-95% amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore, a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two amino acid sequences would occur by chance.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in any particular described sequence.

EXAMPLES

The following examples are offered to illustrate, but not to limit the claimed invention.

Example 1

This Example sets forth materials and methods used in the studies reported herein.

Alignment of protein sequences. The *S. solfataricus* ssb sequence (SSO2364) encoding the SSB protein (SsoSSB) was identified using BLASTP at the *S. solfataricus* genome website: (archbac.u-psud.fr/projects/sulfolobus). The *A. pernix* ssb sequence (gi5105001) encoding the SSB protein (ApeSSB) was identified using BLAST at the PEDANT website: (pedant.gsf.de). Both open reading frames were recognized through their homology to MJ1159, encoding the *Methanococcus jannaschii* RPA protein (Chedin, F. et al., *Trends Biochem Sci* 23:273-277 (1998)). Subsequent alignments were performed using the ALIGN program at websitr toulouse.inra.fr/multalin.html and additional features were highlighted by manual adjustment. BestFit comparisons were performed using the Wisconsin Package Version 10.1, Genetics Computer Group (GCG), Madison, Wisconsin and were between *S. cerevisiae* RPA70 single-stranded DNA-binding region 1 (gi6319321, amino acids 301-399) and the following single-stranded DNA-binding protein sequences; *Archaeoglobus fulgidus* (gi11497994), *A. pernix* (gi5105001), *Bacillus subtilis* (gi2127217), *Escherichia coli* (gi134913) *Homo sapiens* (gi1350579), *M. jannaschii* (MJ1159), *Methanobacterium thermoautotrophicum* (gi2622495), *Pyrococcus abyssii* (gi5457718), *Pyrococcus* horikoshii (gi3258332), *S. solfataricus* (SS02364), as well as between *E. coli* SSB protein (gi134913) and *S. solfataricus* (S S02364). The *A. fulgidus* sequence used was one of two identified as homologous to MJ1159 and is the most homologous to the N-terminus of the *M. jannaschii* protein (Chedin 1998). The *M. thermoautotrophicum* sequence was adjusted to account for the frameshift identified by Chedin 1998.

Strains and cultivation. *S. solfataricus* strain P2 (DSM 1616, (Zillig, W. et al., Arch *Microbiol* 125:259-269 (1980)) was the generous gift of Dennis Grogan (University of Cincinnati) and was grown at 80° C. as described (Rolfsmeier, M. et al., *J Bacteriol* 180:1287-1295 (1998)) at a pH of 3.0 in screw cap flasks as described (Rolfsmeier, M. et al., *J Bacteriol* 177:482-485 (1995)). Basal salts medium was Allen's medium (Allen M. B., *Arch. Mikrobiol.*, 32:270-277 (1959)) as modified by Brock (Brock, T. D. et al., *Arch Mikrobiol* 84:54-68 (1972)) and was supplemented with tryptone to a final concentration of 0.2% (w/v). Growth was monitored spectrophotometrically at a wavelength of 540 nm. *Escherichia coli* strains were DH5α (φ80d/acZΔ15, endA1, recA1, hsdR17 ($r_k^{31}$,$m_k^+$), supE44, thi-1, gyrA96, relA1, Δ(lacZY A-argF)U169); BL21(DE3) (ompT [lon] hsdS$_B$ ($r_B^-m_B^-$); an *E. coli* B strain) with DE3, a λ prophage carrying the T7 RNA polymerase gene); and KLC789 (F", metA7, rha8, thyA36, amp50, deoC2, ssb-1) (Chase, J. W. et al., *J Mol Biol* 164:193-211 (1983)) from laboratory collections or BL21(DE3) CodonPlus ultracompetent cells from Stratagene. *E. coli* was propagated in LB medium (Sambrook, J. et al., *Molecular cloning: a laboratory manual.* Cold Spring Harbor, N.Y.: Cold Spring Harbor Laboratory Press (1989)) at 30° C. in Ehrlenmeyer flasks shaken at 250 rpm.

PCR amplification and cloning of the SsoSSB gene. Genomic DNA was prepared from *S. solfataricus* cells as previously described (Rolfsmeier, M. et al., *J Bacteriol* 180:1287-1295 (1998)). PCR was performed using 10 mM potassium chloride, 10 mM ammonium sulfate, 2 mM magnesium chloride, 20 mM Tris-Cl (pH 8.75), 0.1% Triton X-100, 100 μM dNTP's, 100 pmol primers, 2 ng template DNA, and 2.5 U of recombinant Pfu DNA polymerase (Stratagene). The primers for amplification of SsoSSB were: 5'-CGGGATCCCCTTTCA TTAACACATAGATT-TATAAATGG-3' (SEQ ID NO:8) (SSB-F) and 5'-CGG-GATCCGGAGCAA GCTCGTATACTTTGTCTCTAGCC-3' (SEQ ID NO:9) (SSB-R). All primer sequences were chosen based on sequence information presented at the *S. solfataricus* genome website: http://www-archbac.u-psud.fr/projects/sulfolobus. PCR was performed using a 55° C. annealing temperature and the resulting PCR products were digested with BamHI and ligated into the BamHI site of pUC19. Ligated molecules were transformed into DH5α as previously described (Rolfsmeier, M. et al., *J Bacteriol* 180:1287-1295 (1998)). Plasmids from transformants were isolated using the Qiagen midiprep system and DNA sequences were determined using BigDye dRhodamine Terminator chemistry (Perkin-Elmer Corp.) at the Division of Biological Sciences Automated DNA sequencing facility at UC Davis.

Overexpression of SsoSSB protein. Sequence information obtained from the pUC19 clones was used to design a forward PCR primer with an NdeI site at the starting ATG codon for SsoSSB. The gene sequence was re-amplified from the cloned template using the new forward primer (5'-GTGAGTCGAGTCATATGGAAG-3') (SEQ ID NO:10) and the original reverse primer. The resulting product was digested using NdeI and BamHI prior to ligation into pET21a (Novagen) that had been digested with the same enzymes to place the gene under the control of the T7 promoter. Ligation products were transformed into the CodonPlus strain (Stratagene) and transformants were cultivated at 30° C. in LB containing 100 μg/ml ampicillin until mid-log phase.

Purification of SsoSSB protein. BL21(DE3) CodonPlus cells (Stratagene) harboring the pET21a SsoSSB expression construct were grown at 30° C. in a 500 ml volume to an $OD_{600}$ of 1.0. IPTG was added to a final concentration of 1 mM and expression was allowed to continue for 2 hours. Cells were harvested by centrifugation and stored at −20° C. until processing. The frozen cell pellet was resuspended in 4 ml of 10 mM Tris-Cl (pH 7.5), 1 mM EDTA (TE) with 50 mM NaCl and sonicated to disrupt the cells. The sonicate was heat treated at 80° C. for 1 hour, and insoluble material was removed by centrifugation. Clarified sonicate was applied to a ssDNA cellulose column equilibrated in 30 mM Tris-Cl (pH 7.5), 1 mM EDTA, 1 mM DTT, and 10% glycerol; the column was washed with the same buffer containing 0.5 M NaCl and 0.75 M NaCl at room temperature. Fractions eluting at 0.75 M NaCl were pooled and dialyzed into buffer containing 20 mM Tris-Cl (pH 7.5), 1 mM DTT, 1 mM EDTA, and 10% glycerol. This material was then applied to a Resource Q column (Pharmacia) equilibrated with the same buffer at room temperature. Protein was eluted using a gradient of 50 mM NaCl to 1 M NaCl in the same buffer; the SsoSSB protein eluted from the column at approximately 60 mM NaCl. The protein was pooled and concentrated by using dry polyethylene glycol and then dialyzed against 25 mM Tris HCl (pH 7.5), 20 mM NaCl, 1 mM EDTA, 1 mM DTT, 10% spectral grade glycerol, and stored at 4° C. Protein concentrations were obtained by spectrophotometric absorbance at a wavelength of 280 nm, using an extinction coefficient of 12660 $M^{-1}$ $cm^{-1}$ as determined with the ProtParam tool at the ExPASy website (http://expasy.cbr.nrc.ca/tools/protparam.html).

Gel filtration of SsoSSB protein. Fast protein liquid chromatography (FPLC) was performed at 4° C. using a Superose 12 column (Pharmacia) and 25 mM Tris HCl pH 7.5, 1 mM DTT, 100 mM NaCl, 1 mM EDTA as the running buffer. Molecular size standards were BSA (66 kDa), carbonic anhydrase (29 kDa), and cytochrome C (12.4 kDa) and were prepared in running buffer. A total of 10 μg of SsoSSB protein was loaded on the column in a volume of 100 μl. Elution profiles were determined by monitoring $OD_{280}$ readings and a standard curve was prepared by plotting Ve/Vo against the molecular mass of the size standards. The value of Vo was determined by elution of dextran blue from the Superose 12 column.

Gel mobility-shift analysis. The 63-mer oligonucleotide 5'-ACAGCACCAAT GAAATCTATTAAGCTCCT-CATCGTCCGCAAAAATATCGTCACCTCAAAAGGA-3' (SEQ ID NO:11) was end-labeled with $^{32}$P using T4 polynucleotide kinase (NEB). SsoSSB protein was incubated at the indicated concentrations with 10 μM (nucleotides) of the $^{32}$P-labeled oligonucleotide for 30 minutes at 75° C. in buffer containing 30 mM TrisOAc (pH 7.5), 10 mM $MgOAc_2$, 5 mM NaCl, 0.1 mM DTT and 50 μg/ml BSA. Increasing concentrations of linearized pUC19 were used as the dsDNA competitor as indicated in the text. Loading dye was then added and the samples were applied to a vertical 10% acrylamide gel prepared with 1×TBE buffer (0.089 M Tris-borate, 0.089 M boric acid, 0.002 M EDTA).

In vivo complementation. The SsoSSB expression vector or pET21a (empty vector) was transformed into *E. coli* strain KLC789 (Chase, J. W. et al., J Mot Blot 164:193-211

(1983)) containing pTara, a T7 polymerase expression vector that is inducible by arabinose addition. The pTara plasmid was the generous gift of Kathleen Mathews (Rice University) (Wycuff, D. R. et al., *Anal Biochem* 277:67-73 (2000)). Transformants were propagated in LB medium lacking yeast extract with 0.2% (w/v) arabinose, 100 µg/ml ampicillin, and 30 µg/ml chloramphenicol for 16 hours at 30° C. to allow phenotypic overexpression of SsoSSB protein. Control cultures were propagated identically, except 0.2% (w/v) glucose was substituted for arabinose. Cells were subcultured into fresh medium without chloramphenicol and grown at 30° C. until they were shifted to the non-permissive temperature of 43° C. Optical densities were monitored spectrophotometrically at a wavelength of 600 nm. Colony forming units (cfu) per milliliter were determined by plating serial dilutions of each timepoint in triplicate on LB medium. Plates were incubated overnight at 30° C. prior to scoring for viable counts.

DNA strand exchange reactions. *E. coli* RecA protein (11 µM) was incubated with ɸX174 ssDNA (New England Biolabs) at a concentration of 33 µM (nucleotides) in 30 mM TrisOAc (pH 7.5), 10 mM DTT, 20 mM MgOAc, 2.5 mM ATP, and 5 µg/ml BSA at 37° C. for 10 minutes. After the addition of either 2.2 µM SsoSSB protein or *E. coli* SSB protein, reaction mixtures were incubated at 37° C. for another 5 min before the introduction of PstI-linearized ɸX174 dsDNA (New England Biolabs) at a concentration of 33 µM (nucleotides). The reaction mixtures were then incubated at 37° C. for 90 minutes and were stopped by the addition of SDS to a final concentration of 0.6% and proteinase K to a final concentration of 1 µg/ml. Deproteinization of the reaction mixtures was carried out at 37° C. for 10 minutes.

Gel electrophoresis. Agarose gels for evaluation of cloning procedures were prepared at 0.8% and run at approximately 150 V in TBE buffer prior to staining with ethidium bromide. Tricine SDS/PAGE, used to monitor protein purification, was prepared with a 4% stacking gel and a 20% separating gel as described (Price, L. B. et al., *J Bacteriol* 182:4951-4958 (2000)) and run at 100 V. Acrylamide gels for gel mobility-shift analysis were prepared at 10% in TBE buffer and run at 100 V for 3 hours at 65° C. prior to exposure to phosphorimaging screens and analysis with a Storm 840 PhosphorImager (Molecular Dynamics). Agarose gels for evaluation of DNA strand exchange products were prepared at 1% and run at approximately 30 V in TAE buffer (0.04 M TrisOAc, 0.002 M EDTA) for 15 hours prior to staining with ethidium bromide.

Example 2

This Example sets forth the results of studies conducted using the methods and materials set forth in the previous Example.

Crenarchaeal homologues of ssDNA binding proteins.

Previous searches of genome sequences identified open reading frames with homology to human RPA70 from the euryarchaeons *M. jannachii*, *M. thermoautrophicum*, and *A. fulgidus* (Chedin, F. et al., *Trends Biochem Sci* 23:273-277 (1998); Kelly, T.J. et al., *Proc Natl Acad Sci USA* 95:14634-14639 (1998)). Each of these sequences consists of multiple ssDNA-binding domains contained in one or a pair of open reading frames, which share a significant degree of sequence homology among themselves. In one case, the protein encoded by this homologous sequence was shown to be an RPA homologue both structurally and functionally (Kelly, T. J. et al., *Proc Natl Acad Sci USA* 95:14634-14639 (1998)). However, there has been no corresponding homologue of RPA identified in members of the other branch of the archaeal domain, the crenarchaea. The availability of sequence information from both *A. pernix* (Kawarabayasi, Y. et al., *DNA Res* 6:83-101;145-152 (1999)) and *S. solfataricus* (She, Q. et al., *Proc Natl Acad Sci USA* 98:7835-7840 (2001)) permitted a search for ssDNA-binding protein sequences in the crenarchaea.

A survey of genome sequences from *A. pernix* and *S. solfataricus* with the program BLAST (Altschul, S.F. et al., *J Mol Biol*, 215:403-410, (1990)) revealed a single small open reading frame in each genome with sequence similarity to MJ1159, the RPA homologue from *M. jannaschii*. Both open reading frames code for proteins that are strikingly similar to the first ssDNA-binding domain of the *M. jannaschii* RPA (FIG. 1a), but are much shorter than the *M. jannaschii* protein. The *S. solfataricus* sequence (SSO2364) is 477 base pairs in length and encodes a protein of 148 amino acids while the *A. pernix* sequence (gi5105001) is 429 base pairs in length and encodes a protein of 143 amino acids; in contrast, the *M. jannaschii* protein is 645 amino acids in length. The *S. solfataricus* protein has a predicted pI of 9.0, and the *A. pernix* protein also has a predicted pI of 9.0. For comparison, the pI's of the T4 phage SSB homologue gp32, *E. coli* SSB, and *M. jannaschii* RPA are 4.8, 5.4, and 4.7 respectively. The *S. solfataricus* protein has 52% similarity and 26% identity with MJ1159 from amino acids 68 to 170 and the *A. pernix* protein has 52% similarity and 25% identity with MJ1159 from amino acid 70 to 173. The two residues conserved in all archaeal sequences correspond to amino acids involved in DNA binding in human RPA70 protein domain B (Thr 359 and Trp 361 in the hsRPA70 sequence) (Bochkarev, A. et al., *Nature*, 385:176-181 (1997)) (FIG. 1a). Additionally, the *S. solfataricus* sequence shares two other amino acids with human RPA70 that are implicated in DNA binding, Phe 386 and Ser 396 (Bochkarev, A. et al., *Nature*, 385:176-181 (1997)).

The two crenarchaeal protein sequences show a remarkable level of homology between each other, exhibiting 69% similarity and 47% identity (FIG. 1). Both of the newly identified open reading frames are significantly shorter than their euryarchaeal and eukaryotic counterparts, each comprising only a single ssDNA-binding region as opposed to closely related tandem repeats (four, in the case of the *M. jannaschii* protein) of multiple binding regions in a larger polypeptide. Examination of nearby regions in each genome revealed no further sequences that might encode for portions of a ssDNA-binding protein, suggesting either that *S. solfataricus* SSO2364 and *A. pernix* gi5105001 are the only genes responsible for producing SSB for these crenarchaeons or that there were other genes elsewhere in the genome that encoded the remainder of the subunits for an RPA-like protein. No other sequence with significant similarity to MJ1159 is apparent elsewhere in the complete genomes of either *A. pernix* or *S. solfataricus*, suggesting that these proteins may serve as the sole SSBs in these organisms.

The crenarchaeal proteins structurally resemble *E. coli* SSB protein.

In contrast to other archaeal SSB homologues which resemble eukaryotic RPAs, it appears that the overall architecture of the crenarchaeal versions is distinctly different. Euryarchaeal RPA homologues are comprised of multiple DNA-binding domains within one or a pair of proteins and presumably function in monomeric or heterodimeric forms, respectively (FIG. 2). The open reading frames from both *A. pernix* and *S. solfataricus*, however, are distinguished by a single core ssDNA-binding domain of about 100 amino acids in length, identical to that observed in eubacterial ssDNA-binding proteins. This suggests that the quaternary structure of the crenarchaeal SSB protein might be analogous to the eubacterial version and could be tetrameric. Additionally, the crenarchaeal proteins lack the C-terminal zinc finger of the euryarchaeal RPAs and instead, contain a number of acidic residues in this region. This is analogous to the C-terminal structure of E. coli SSB, which is required for protein-protein interactions (Chase, J. W. et al., J. Biol Chem 260:7214-7218 (1985); Kelman, Z. et al., EMBO J17:2436-2449 (1998); Williams, K. R. et al., J Biol Chem 258:3346-3355 (1983)). Also absent in the crenarchaeal sequences is an approximately 100 residue N-terminal region found in euryarchaeal RPAs that is believed to be involved in protein binding (Wold, M. S. Annu Rev Biochem 66:61-92 (1997)).

The SSB protein homologue of phage T4, gp32, has little sequence homology to bacterial SSBs but displays both structural similarity with these proteins and an acidic C-terminus (Shamoo, Y. et al., Nature 376:362-366 (1995)). Much like gp32, however, the crenarchaeal SSBs share minimal sequence homology with E. coli SSB. BestFit alignment of the crenarchaeal sequences with E. coli SSB shows 35% similarity and 31% identity over only 48 amino acids for SsoSSB and 43% similarity and 38% identity over only 60 amino acids for ApeSSB. However, the crenarchaeal proteins do appear to share structural similarity with the eubacterial protein. Despite reduced sequence homology with E. coli SSB, homology-dependent modeling of the expected structure for S. solfataricus SSB reveals striking similarity between the two proteins in the core DNA binding region; a similar analysis was used to confirm the previous identification of the euryarchaeal RPA homologues. The modeling shows strong evolutionary structural conservation of the OB-fold (residues 32-71) which is implicated in DNA binding, as well as the a-helix, which is involved in subunit interactions (Webster et al, FEBS Lett, 411:313-316 (1997)). Equivalent modeling using hsRPA70 also demonstrated strong structural conservation, especially with the RPA-B subdomain. These results confirm that the open reading frame from S. solfataricus encodes a ssDNA-binding protein.

Expression and purification of the SSB homologue from S. solfataricus.

Figure 3:
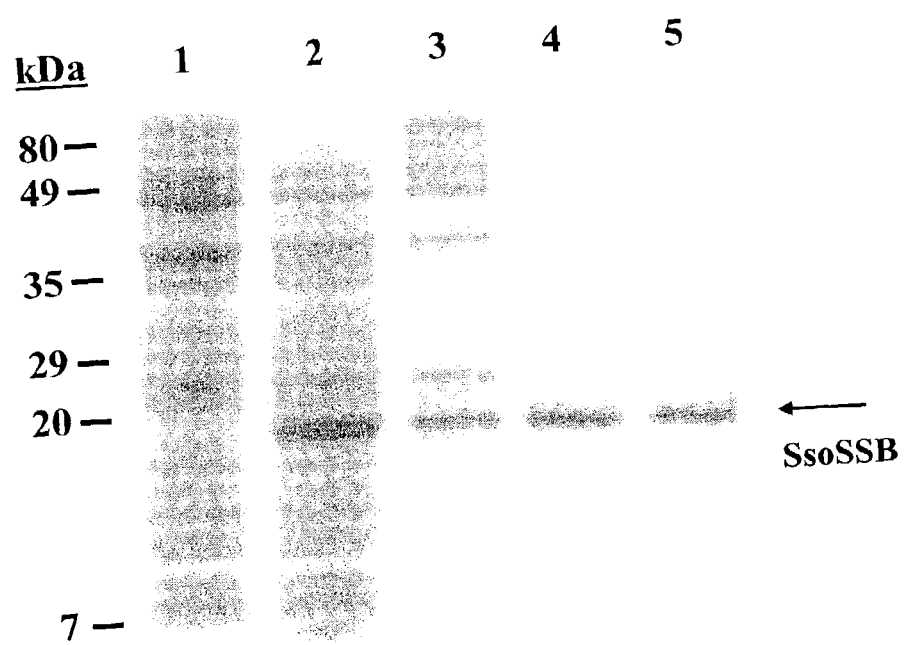
FIG. 3. SDS-PAGE of the purified SsoSSB protein. Samples were subjected to SDS-PAGE and gels were stained with Coomassie brilliant blue R250. The samples loaded were: uninduced crude cell sonicate (lane 1, 100 µg protein); induced crude cell sonicate (lane 2, 100 µg protein); heat-treated clarified sonicate (lane 3, 80 µg protein); pooled ssDNA-cellulose fractions (lane 4, 15 µg protein); and concentrated Resource Q fractions (lane 5, 15 µg protein). The arrow indicates the position of the SsoSSB protein.

To determine if SSO2364 from S. solfataricus did indeed encode a functional SSB protein homologue, we purified and characterized the candidate protein. The SSO2364 open reading frame was cloned into the pET21a bacterial expression vector and subsequently heterologously expressed in E. coli. The bacterial strain carried a plasmid encoding three rare tRNA genes in an effort to reduce translational pausing as the predicted protein sequence contains 11 codons that are rare in E. coli, four of which are present in the final 50 bases of the open reading frame. The expressed protein is soluble and was purified to near homogeneity by first heat-treating the cell sonicate at 80° C. to denature all mesophilic proteins. This step was followed by affinity chromatography on ssDNA-cellulose, and by anion exchange chromatography on Resource Q. The recombinant protein eluted from ssDNA-cellulose at 0.75 M NaCl, which is identical to the salt concentration necessary for elution of E. coli SSB (Lohman, T. M. et al., Biochemistry 25:21-25 (1986)). In contrast, elution of either yeast or M jannachii RPA from the same matrix requires 1.5 M NaCl with the addition of 40% ethylene glycol, 1.3 M potassium thiocyanate, or 1.5 M sodium thiocyanate (Henricksen, L. A. et al., J Biol Chem 269:24203-24208 (1994); Heyer, W. D. et al., Embo J 9:2321-2329 (1990); Kelly, T. J. et al., Proc Natl Acad Sci USA 95:14634-14639 (1998)), suggesting that the S. solfataricus SSB (SsoSSB) protein is chemically more similar to the bacterial protein than it is to RPA. The SsoSSB protein eluted at approximately 60 mM NaCl from Resource Q and pooled fractions yielded essentially pure protein (greater than 98% purity based on Coomassie stained gels). Examination of the purified protein by SDS/PAGE revealed a single band with a molecular weight of approximately 16 kDa, in close agreement with the predicted molecular weight of 16,138 D as determined from the amino acid sequence (FIG. 3).

The SsoSSB protein forms tetramers in solution.

Figure 4A:
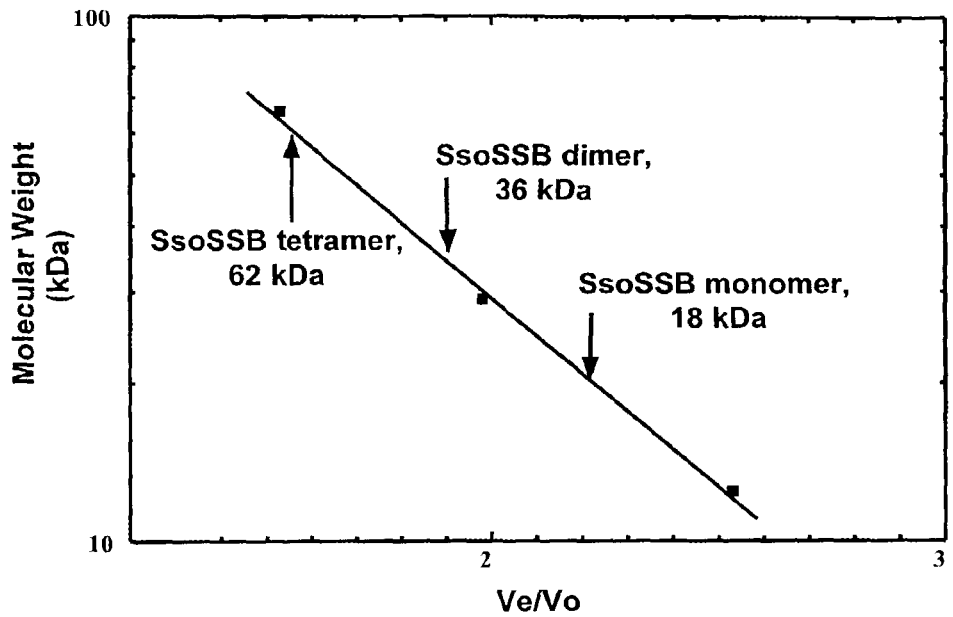
FIGS. 4A and 4B consist of, showing gel filtration chromatography of SsoSSB protein.
Figure 4B:
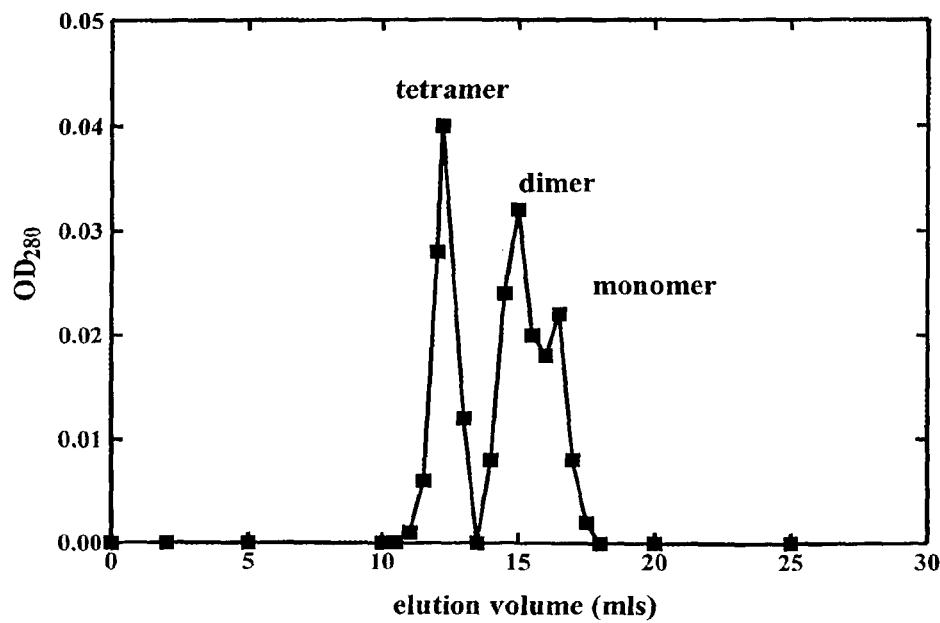

It was of interest to determine if the purified S. solfataricus protein would multimerise in solution. Analytical gel filtration was used to determine the native form of the recombinant protein. Examination of the SsoSSB protein in solution revealed that it was present in three distinct species: monomeric, dimeric, and tetrameric forms, at 18 kDa, 36 kDa, and 62 kDa, respectively (FIG. 4a). As demonstrated by a representative elution profile (FIG. 4b), the composition of the purified material was primarily tetrameric, while somewhat less dimeric protein was present. A significantly smaller quantity of the monomeric form of SsoSSB protein was observed. This result indicates that the SsoSSB protein indeed forms tetramers in solution. The M. jannachii RPA protein does not multimerize in solution (Kelly, T. J. et al., Proc Natl Acad Sci USA 95:14634-14639 (1998))).

SsoSSB protein binds ssDNA.

Figure 5:
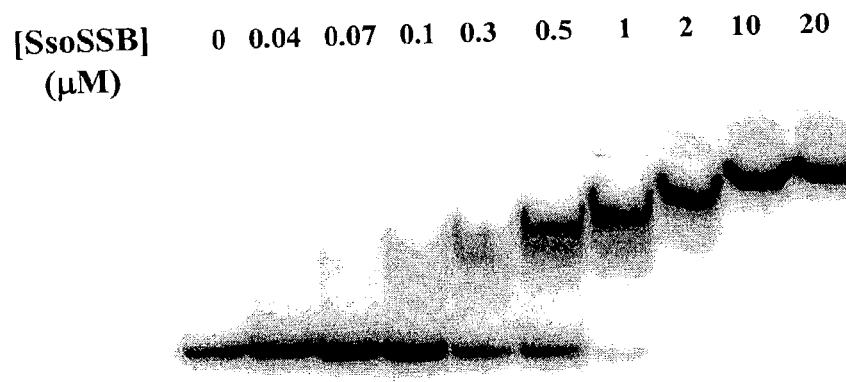
FIG. 5. Gel mobility-shift analysis of SsoSSB protein binding to ssDNA. Increasing concentrations of protein (0.04 µM to 20 µM) were added to a constant concentration of 63-mer oligonucleotide (10 µM nucleotides).

To determine the occluded binding site size of the protein and to evaluate the activity of the SsoSSB protein, we performed acrylamide gel mobility-shift assays with a radioactively labeled single-stranded oligonucleotide that was 63 nucleotides in length (FIG. 5). When a fixed quantity of radiolabeled oligonucleotide was incubated with increasing quantities of protein, a band of reduced mobility was observed. The apparent mobility further decreased upon addition of more protein, finally achieving a constant mobility after the addition of 2 μM protein. The absence of discrete species implied rapid equilibration between bound and free forms of the complexes, and consistent with this possibility, more discrete species were visualized when electrophoresis was performed more rapidly (at high voltage). The addition of linear pUC19 DNA to a 100-fold molar (nucleotide) did not alter the mobility-shift pattern, demonstrating that the SsoSSB has an, at least, 100-fold greater affinity for ssDNA than for dsDNA. Saturation was achieved at a ratio of approximately one SSB protein molecule to 5 nucleotides. The M. jannaschii RPA protein has a site size of 15 to 20 nucleotides (Kelly, T. J. et al., Proc Natl Acad Sci USA 95:14634-14639 (1998)) whereas the site size of E. coli SSB protein, depending on solution conditions, varies from 8 to 16 nucleotides per monomer. The apparent site size of SsoSSB protein is similar to the 7 nucleotide site size observed for phage T4 SSB protein, gp32. Binding of SsoSSB protein to ssDNA does not appear to be a cooperative process under these conditions, as intermediately shifted species are evident instead of the approximately 2-state transitions that typify cooperative binding. Rather, a steady reduction in the mobility of protein-DNA complexes occurs as protein concentration is increased, suggesting that binding of SsoSSB protein to ssDNA is distributive in nature. The observed band-retardation pattern is likely the result of a combination of this non-cooperative binding and rapid equilibration of protein-DNA complexes during electrophoresis.

SsoSSB protein is a functional SSB homologue.

Figure 6A:
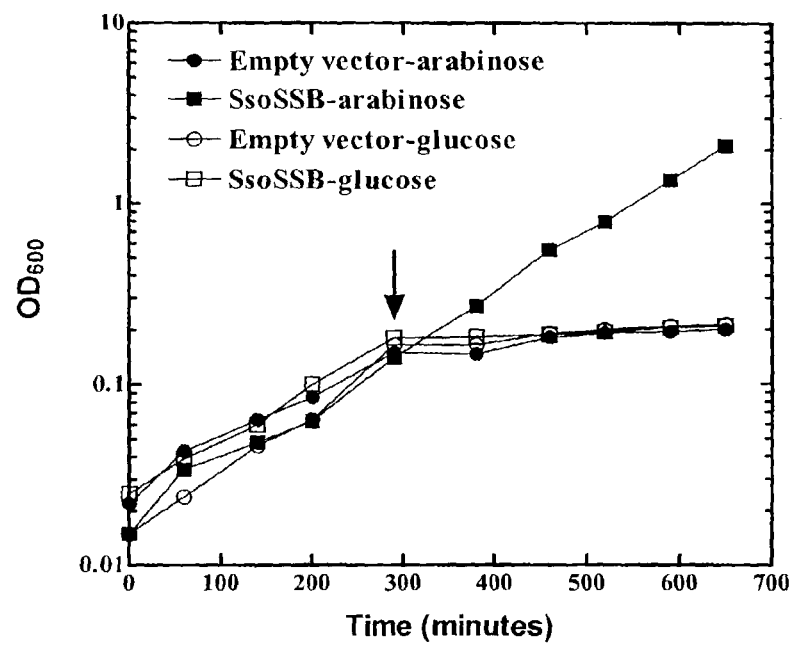
FIGS. 6A and 6B consist of, and shows that overexpression of SsoSSB protein rescues the lethal phenotype of an *E. coli* ssb-1 mutation. Both Figures: KLC789 cells containing the pTara arabinose-inducible T7 expression plasmid, and either pET21a (circles) or the SsoSSB expression vector (squares) were grown at 30° C. in either arabinose (closed symbols) or glucose (open symbols). Cultures were shifted to 43° C. at the point indicated by the arrow.
Figure 6B:
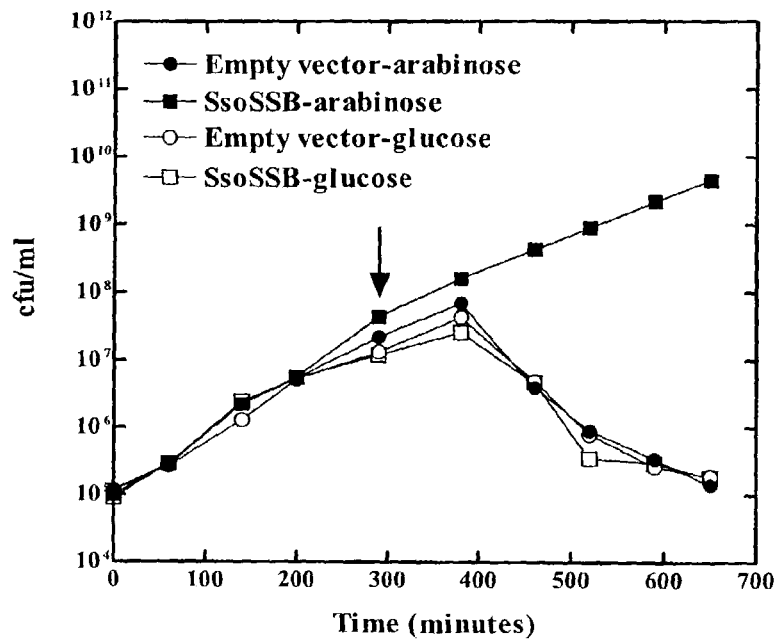

In *E. coli*, SSB is an essential protein. A number of mutations were used to elucidate the function of *E. coli* SSB protein; one mutation is the temperature sensitive mutation called ssb-1. The ssb-1 mutation is an alteration of amino acid 55 from a histidine to a tyrosine that is believed to destabilize the tetrameric SSB protein complex upon shifting temperature from 30° C. to the non-permissive temperature of 43° C., resulting in a lethal phenotype (Chase, J. W. et al., *J Mol Biol* 164:193-211 (1983)). Overexpression of wild-type *E. coli* SSB protein encoded on a plasmid can overcome the lethality of the mutation (Chase, J. W. et al., *J Mol Biol* 164:193-211 (1983)) as can the SSB protein of bacteriophage P1 (Lehnherr, H. et al., *J Bacteriol* 181:6463-6468 (1999)). To test the in vivo functionality of SsoSSB, the protein was overexpressed in the *E. coli* strain KLC789, which carries the ssb-1 allele. The SsoSSB plasmid was transformed into KLC789 along with a plasmid carrying an arabinose-inducible T7 polymerase gene. Cells were grown in the presence of arabinose for 16 hours at the permissive temperature to allow over-expression of the SsoSSB protein, while control cultures were cultivated in the presence of glucose. Cells were then shifted to the non-permissive temperature and monitored for further growth (FIG. 6a). The presence of the open reading frame encoding SsoSSB protein in pET21a permitted continued growth of the ssb-1 mutant strain while the pET21a vector alone was unable to rescue the lethal phenotype. Rescued growth required the presence of arabinose, as control experiments with glucose showed no increase in optical density that would be consistent with continued growth. To verify that the cells containing the SsoSSB plasmid were indeed still growing, viable counts for each timepoint were determined by plating (FIG. 6b). Following the temperature shift, the control cultures continued to grow for a brief period and then dramatically lost viability. In contrast, the cells containing the SsoSSB plasmid displayed a continuous increase in viable counts. These results indicate that SsoSSB protein is capable of replacing *E. coli* SSB protein in vivo and that it functions at 43° C.

SsoSSB protein stimulated DNA strand exchange by *E. coli* RecA protein.

Figure 7A:
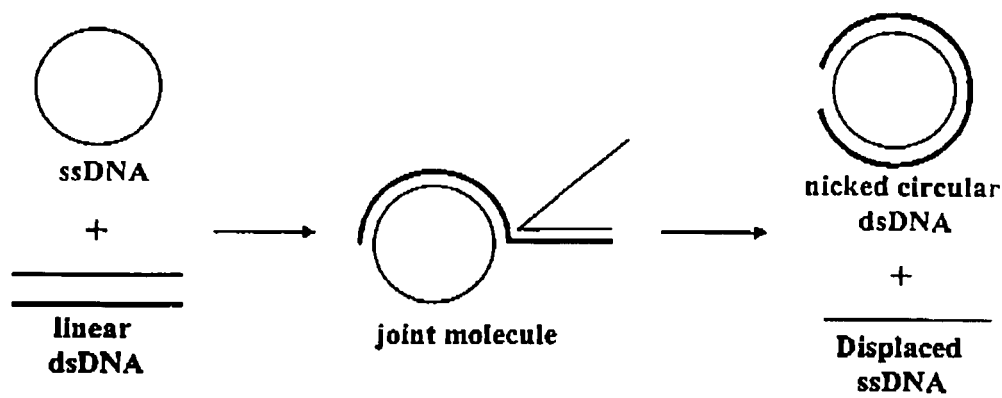
FIGS. 7A and 7B consist of and shows that SsoSSB protein stimulates DNA strand exchange by *E. coli* RecA protein.
Figure 7B:
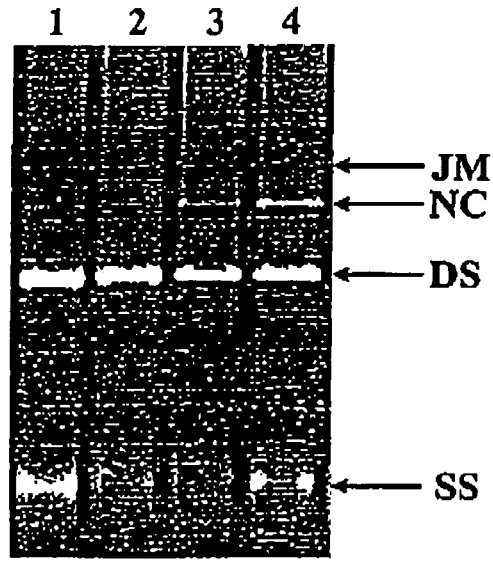

It was previously shown that heterologously expressed SSB proteins can stimulate DNA strand exchange mediated by *E. coli* RecA protein (Egner, C. et al., *J Bacteriol* 169:3422-3428 (1987)). To demonstrate the functionality of the SsoSSB protein in at least one nucleic acid metabolic function in vitro, DNA strand exchange reactions were performed (FIG. 7). Purified SsoSSB protein was capable of substituting for *E. coli* SSB protein in DNA strand exchange reactions mediated by *E. coli* RecA protein at 37° C. using homologous φX174 ss- and dsDNA. Clear enhancement of DNA strand exchange, as determined by production of nicked circular product, was observed with SsoSSB protein (FIG. 7, lane 3). Interestingly, the *M. jannaschii* RPA protein can also promote RecA-mediated DNA-strand exchange. The reduced amount of nicked circular product in reactions containing SsoSSB protein relative to levels with *E. coli* SSB protein may be the result of performing the experiment at temperatures where SsoSSB protein is not as effective. The optimal temperature for the SsoSSB protein is expected to be near the growth temperature of *S. solfataricus*, which is 80° C. As yet, no enhancement of strand exchange activity through addition of SsoSSB protein to *S. solfataricus* RadA protein-containing reactions at high temperature has been observed, though this may be a consequence of inappropriate assay conditions or may signify a post-synaptic role for SsoSSB protein at physiological temperatures.

Example 3

This Example discusses the results of the studies set forth above.

Divergence between the archaeal and eukaryotic lineages is more recent than the divergence of the bacterial and eukaryotic/archaeal groups (Olsen, G. J. et al., *Cell* 89:991-994 (1997)). Accordingly, a number of features shared by eukaryotes and archaea, but not bacteria, including replication and transcription proteins were likely obtained after evolutionary divergence of these three groups. In contrast, features found in archaea and bacteria but not in eukaryotes including morphological attributes (a lack of organelles and nucleus), coupling of transcription and translation, conjugative mechanisms, and a single circular genome may be reminiscent of a more ancient, shared ancestor.

However, despite the logic of this viewpoint, the evolutionary behavior of the archaea is not so simplistic. Our results indicate that, in contrast to the canonical expectation that all archaeal ssDNA binding proteins would be RPA-like, the crenarchaeal SSBs share sequence homology with eukaryal RPAs but structural homology with bacterial SSBs. Homology-dependent modeling of SsoSSB demonstrates conservation of the OB-fold, indicative of ssDNA binding proteins. Both *E. coli* SSB and SsoSSB proteins elute from ssDNA-cellulose at the same salt concentration, and both form tetramers in solution. The apparent binding site size is approximately 5 nucleotides, which is consistent with the site size observed for T4 g32 protein and the low site size binding mode of *E. coli* SSB protein, but is one-fourth that of *M. jannachii* RPA protein, which has four DNA-binding domains. Another feature that makes the crenarchaeal SSB protein more eubacterial is that SsoSSB protein and ApeSSB protein are missing the zinc finger motif near the C-terminus which is present in both euryarchaeal and eukaryal RPAs, suggesting that this motif was acquired after the separation of the two archaeal branches. Furthermore, the acidic residues in the SsoSSB protein C-terminal region are similar to those found in bacterial proteins and may have been maintained from the last shared bacterial and archaeal ancestor. SsoSSB protein resembles *E. coli* SSB chemically in that they both elute from ssDNA-cellulose at 0.75 M NaCl while the euryarchaeal and eukaryal RPAs require higher salt concentrations and the addition of ethylene glycol, potassium thiocyanate, or sodium thiocyanate for elution from this matrix. Finally, SsoSSB protein can functionally substitute for *E. coli* SSB protein both in vivo and in vitro. In vivo, overexpression of the SsoSSB protein can overcome the lethal ssb-1 temperature-sensitive mutation in *E. coli*; in vitro, the SsoSSB protein can replace the *E. coli* SSB protein in DNA strand exchange reactions mediated by RecA protein.

Concurrent with our efforts, the same crenarchaeal protein was identified by another laboratory using biochemical criteria (Wadsworth, R. I. et al., *Nucleic Acids Res* 29:914-920 (2001)). No multimerisation of the protein was demonstrated, contrary to our observation. In our experience, however, heating of the SsoSSB protein is necessary for formation of the tetrameric structure as observed by gel filtration and for activity in DNA strand-exchange. The absence of this heating step by Wadsworth and White could account for their failure to observe tetramers.

Overall, the archaeal ssDNA binding proteins show more sequence similarity to eukaryotic RPA proteins than to *E. coli* SSB protein. However, the common sequences and DNA-binding domain utilization hint at a conserved evolutionary relationship between RPA and SSB (FIG. 2). Strong homology among the archaeal proteins suggests a common evolutionary origin, and the crenarchaeal SSB proteins may represent a link to ancient ssDNA-binding proteins. The crenarchaeal SSB protein, being one of the simplest in structure, may represent the earliest form of single-stranded DNA-binding proteins involved in recombination and, it may serve as a model for understanding structure, function, and evolution of the conserved core ssDNA-binding domain.

Crenarchaea and euryarchaea are distinguished from each other not only by single-stranded DNA-binding proteins as described here, but also by double-stranded DNA-binding proteins. While eukaryotic-like histone proteins have been identified and extensively studied in members of the euryarchaea (Sandman, K. et al., *Arch Microbiol* 173:165-169 (2000)), no such homologues are apparent in members of the crenarchaea. Instead, crenarchaea maintain sequences that code for small, basic dsDNA-binding proteins (Agback, P. et al., *Nat Struct Biol,* 5:579-584 (1998)); Faguy, D. M. et al., *Curr Biol* 9:R883-886 (1999)). These proteins are proposed to be comparable to histone-like proteins in eubacteria, especially Sso7d which was shown to be analogous to HU (Lopez-Garcia, P. et al., *Nucleic Acids Res* 26:2322-2328 (1998). It appears that the crenarchaea have maintained both single-stranded and double-stranded DNA-binding proteins that are more similar to those found in bacteria than they are to eukaryotic homologues. Crenarchaeal dsDNA-binding proteins and SSB may have evolved separately from mechanisms employed by eukaryotes or, alternatively, crenarchaea diverged earlier, prior to the co-evolution of eukaryotic-like histones and RPA. The use of a eubacterial-like SSB may necessitate a eubacterial DNA-binding protein for the compaction of DNA. The discovery of an SSB homologue in the crenarchaea that is significantly more similar to eubacterial SSB both structurally and biochemically than it is to either euryarchaeal or eukaryotic RPA further establishes the evolutionary distance between the two archaeal phyla.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for performing a nucleic acid amplification reaction, said method comprising: (1) contacting and binding a single stranded DNA with a multimeric protein in a nucleic acid amplification reaction; and (2) performing the nucleic acid amplification reaction, wherein each unit of said multimeric protein has at least 95% sequence identity to SEQ ID NO:1, and wherein said multimeric protein binds said single stranded DNA.

2. The method of claim 1, wherein each unit of said multimeric protein has the sequence of SEQ ID NO:1.

3. The method of claim 1, wherein said nucleic acid amplification is selected from the group consisting of polymerase chain reaction (PCR), ligase chain reaction, transcription-based amplification system, and self-sustained sequence replication system.

4. The method of claim 3, wherein the nucleic acid amplification is polymerase chain reaction (PCR).

5. A method for performing a nucleic acid engineering reaction, said method comprising: (1) contacting and binding a single stranded DNA with a multimeric protein in a nucleic acid engineering reaction; and (2) performing the nucleic acid engineering reaction, wherein each unit of said multimeric protein has at least 95% sequence identity to SEQ ID NO:1, and wherein said multimeric protein binds said single stranded DNA.

6. The method of claim 5, wherein each unit of said multimeric protein has the sequence of SEQ ID NO:1.

7. The method of claim 5, wherein said nucleic acid engineering is selected from the group consisting of PCR-based DNA sequencing, recombination mediated cloning, PCR-mediated gene replacement, PCR-mediated recombination, RT-PCR cDNA synthesis, and in vitro sequence mutagenesis.

8. The method of claim 1, wherein in step (1) DNA strand exchange is increased.

9. The method of claim 1, wherein yield of said nucleic acid amplification is increased.

10. The method of claim 4, wherein the PCR is reverse transcription PCR (RT-PCR).

11. The method of claim 5, wherein in step (1) DNA strand exchange is increased.

12. The method of claim 5, wherein yield of said nucleic acid engineering is increased.

\* \* \* \* \*

SEQUENCE LISTING

```
<160> NUMBER OF SEQ ID NOS: 12

<210> SEQ ID NO 1
<211> LENGTH: 148
<212> TYPE: PRT
<213> ORGANISM: Sulfolobus solfataricus
<220> FEATURE:
<223> OTHER INFORMATION: single-stranded (ssDNA) binding protein (SSB)
      SSO2364 (SsoSSB)

<400> SEQUENCE: 1

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Arg Gly Phe Arg Gly Gly
        115                 120                 125

Gly Arg Arg Tyr Gly Arg Arg Gly Gly Arg Arg Gln Glu Asn Glu Glu
    130                 135                 140

Gly Glu Glu Glu
145

<210> SEQ ID NO 2
<211> LENGTH: 447
<212> TYPE: DNA
```

```
<213> ORGANISM: Sulfolobus solfataricus
<220> FEATURE:
<223> OTHER INFORMATION: single-stranded (ssDNA) binding protein (SSB)
      SSO2364 (SsoSSB)

<400> SEQUENCE: 2
atggaagaaa aagtaggtaa tctaaaacca aatatggaaa gcgtaaatgt aaccgtaaga    60
gttttggaag caagcgaagc aagacaaata cagacaaaga acggtgttag aacaatcagt   120
gaggctattg ttggagatga aacgggaaga gtaaagttaa cattatgggg aaaacatgca   180
ggtagtataa agaaggtca agtggtaaag atagaaaacg cgtggaccac cgcttttaag   240
ggtcaagtac agttaaatgc tggaagcaaa actaagatag ctgaagcttc agaagatgga   300
tttccagaat catctcaaat accagaaaat acaccaacag ctcctcagca aatgcgtgga   360
ggaggaagag gattccgcgg tgggggaaga aggtatggaa gaagaggtgg tagaagacaa   420
gaaaacgaag aaggtgaaga ggagtga                                       447

<210> SEQ ID NO 3
<211> LENGTH: 93
<212> TYPE: PRT
<213> ORGANISM: Sulfolobus solfataricus
<220> FEATURE:
<223> OTHER INFORMATION: single-stranded (ssDNA) binding protein (SSB)
      SSO2364 (SsoSSB) ssDNA-binding domain

<400> SEQUENCE: 3

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile
                85                  90

<210> SEQ ID NO 4
<211> LENGTH: 88
<212> TYPE: PRT
<213> ORGANISM: Aeropyrum pernix
<220> FEATURE:
<223> OTHER INFORMATION: single-stranded (ssDNA) binding protein (SSB)
      (ApeSSB) ssDNA-binding domain

<400> SEQUENCE: 4

Met Asp Leu Arg Glu Gly Leu Arg Asn Val Ser Ile Ser Gly Arg Val
1               5                   10                  15

Leu Glu Thr Gly Glu Pro Lys Met Val Glu Thr Lys Arg Gly Pro Ala
            20                  25                  30

Thr Leu Ser Glu Ala Val Val Gly Asp Glu Ser Gly Arg Val Lys Val
        35                  40                  45

Thr Leu Trp Gly Ser His Ala Gly Thr Leu Lys Glu Gly Glu Ala Val
    50                  55                  60

Arg Ile Glu Gly Ala Trp Thr Thr Ser Tyr Arg Gly Lys Val Gln Val
65                  70                  75                  80

Asn Val Gly Arg Glu Ser Thr Ile
```

-continued

<210> SEQ ID NO 5
<211> LENGTH: 91
<212> TYPE: PRT
<213> ORGANISM: Methanococcus jannaschii
<220> FEATURE:
<223> OTHER INFORMATION: MJ1159, replication protein A (RPA)
      ssDNA-binding domain

<400> SEQUENCE: 5

Ile Ser Asp Ile Glu Glu Gly Gln Ile Gly Val Glu Ile Thr Gly Val
1               5                   10                  15

Ile Thr Asp Ile Ser Glu Ile Lys Thr Phe Lys Arg Arg Asp Gly Ser
            20                  25                  30

Leu Gly Lys Tyr Lys Arg Ile Thr Ile Ala Asp Lys Ser Gly Thr Ile
        35                  40                  45

Arg Met Thr Leu Trp Asp Asp Leu Ala Glu Leu Asp Val Lys Val Gly
    50                  55                  60

Asp Val Ile Lys Ile Glu Arg Ala Arg Ala Arg Lys Trp Arg Asn Asn
65                  70                  75                  80

Leu Glu Leu Ser Ser Thr Ser Glu Thr Lys Ile
                85                  90

<210> SEQ ID NO 6
<211> LENGTH: 99
<212> TYPE: PRT
<213> ORGANISM: Saccharomyces cerevisiae
<220> FEATURE:
<223> OTHER INFORMATION: replication protein A (RPA70) ssDNA-binding
      domain

<400> SEQUENCE: 6

Asn Phe Ile Lys Leu Asp Ala Ile Gln Asn Gln Glu Val Asn Ser Asn
1               5                   10                  15

Val Asp Val Leu Gly Ile Ile Gln Thr Ile Asn Pro His Phe Glu Leu
            20                  25                  30

Thr Ser Arg Ala Gly Lys Lys Phe Asp Arg Arg Asp Ile Thr Ile Val
        35                  40                  45

Asp Asp Ser Gly Phe Ser Ile Ser Val Gly Leu Trp Asn Gln Gln Ala
    50                  55                  60

Leu Asp Phe Asn Leu Pro Glu Gly Ser Val Ala Ala Ile Lys Gly Val
65                  70                  75                  80

Arg Val Thr Asp Phe Gly Gly Lys Ser Leu Ser Met Gly Phe Ser Ser
                85                  90                  95

Thr Leu Ile

<210> SEQ ID NO 7
<211> LENGTH: 100
<212> TYPE: PRT
<213> ORGANISM: Homo sapiens
<220> FEATURE:
<223> OTHER INFORMATION: replication protein A 70 kDa DNA-binding
      subunit (RPA70) ssDNA-binding domain

<400> SEQUENCE: 7

Asp Phe Thr Gly Ile Asp Asp Leu Glu Asn Lys Ser Lys Asp Ser Leu
1               5                   10                  15

Val Asp Ile Ile Gly Ile Cys Lys Ser Tyr Glu Asp Ala Thr Lys Ile
            20                  25                  30

Thr Val Arg Ser Asn Asn Arg Glu Val Ala Lys Arg Asn Ile Tyr Leu
         35                  40                  45

Met Asp Thr Ser Gly Lys Val Val Thr Ala Thr Leu Trp Gly Glu Asp
 50                  55                  60

Ala Asp Lys Phe Asp Gly Ser Arg Gln Pro Val Leu Ala Ile Lys Gly
 65                  70                  75                  80

Ala Arg Val Ser Asp Phe Gly Gly Arg Ser Leu Ser Val Leu Ser Ser
                 85                  90                  95

Ser Thr Ile Ile
         100

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence:PCR
      amplification forward primer SSB-F

<400> SEQUENCE: 8
cgggatcccc tttcattaac acatagattt ataaatgg                          38

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence:PCR
      amplification reverse primer SSB-R

<400> SEQUENCE: 9
cgggatccgg agcaagctcg tatactttgt ctctagcc                          38

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:new PCR
      forward primer for reamplification from cloned template

<400> SEQUENCE: 10
gtgagtcgag tcatatggaa g                                            21

<210> SEQ ID NO 11
<211> LENGTH: 63
<212> TYPE: DNA
<213> ORGANISM: Artificial Sequence
<220> FEATURE:
<223> OTHER INFORMATION: Description of Artificial Sequence:63-mer
      oligonucleotide end-labeled with 32-P

<400> SEQUENCE: 11
acagcaccaa tgaaatctat taagctcctc atcgtccgca aaaatatcgt cacctcaaaa   60
gga                                                                63

<210> SEQ ID NO 12
<211> LENGTH: 4
<212> TYPE: PRT
<213> ORGANISM: Artificial Sequence

```
<220> FEATURE:
<223> OTHER INFORMATION: Description of Artificial Sequence:consensus
      peptide

<400> SEQUENCE: 12

Thr Leu Trp Gly
1
```